(12) United States Patent
Tran

(10) Patent No.: US 6,807,473 B1
(45) Date of Patent: Oct. 19, 2004

(54) ROAD RECOGNITION SYSTEM

(75) Inventor: Vinh H. Tran, Farmington Hills, MI (US)

(73) Assignee: Continental Teves, Inc., Auburn Hills, MI (US)

( * ) Notice: Subject to any disclaimer, the term of this patent is extended or adjusted under 35 U.S.C. 154(b) by 0 days.

(21) Appl. No.: 10/409,861

(22) Filed: Apr. 9, 2003

(51) Int. Cl.[7] .............................................. B60T 7/12
(52) U.S. Cl. ........................................ 701/80; 701/71
(58) Field of Search ............................. 701/80, 71, 82, 701/91; 340/436, 903; 180/169

(56) References Cited

U.S. PATENT DOCUMENTS

| | | | |
|---|---|---|---|
| 5,864,056 A | 1/1999 | Bell et al. ..................... 73/146 |
| 5,963,148 A | 10/1999 | Sekine et al. ............... 340/905 |
| 6,266,600 B1 | 7/2001 | Miyazaki ..................... 701/71 |
| 6,300,865 B1 | 10/2001 | Fechner et al. ............ 340/436 |
| 6,538,578 B1 * | 3/2003 | Doherty ...................... 340/905 |
| 6,617,980 B2 * | 9/2003 | Endo et al. ................. 340/905 |

* cited by examiner

Primary Examiner—Marthe Y. Marc-Coleman

(57) ABSTRACT

An apparatus and method for detecting the road condition for use in a motor vehicle. The system and method detect road data through a temperature sensor, an ultrasonic sensor, and a camera. The road data is filtered for easier processing. A comparison of the filtered road data to reference data is made, and a confidence level of that comparison is generated. Based on the comparison of filtered road data to reference data, the road condition is determined. The driver may be informed and/or stability control systems may be adjusted based on the detected road surface condition.

21 Claims, 4 Drawing Sheets

ROAD RECOGNITION SYSTEM

FIELD OF THE INVENTION

The present invention relates generally to a road recognition system for detecting the road condition ahead of a motor vehicle, and more particularly relates to a system using image processing to inform the driver and optimize braking performance based on the detected road condition.

BACKGROUND OF THE INVENTION

Many different devices and methods have been employed to determine road condition, and more specifically the surface condition or coefficient of friction between a vehicle tire and the road. For example, various structures have been developed that are formed directly into the tire of a vehicle. Typically, these structures come into contact with the road for detecting the surface coefficient of friction. Unfortunately, such systems require complex structures which can be difficult to apply to existing tires. Further, application directly to the tire makes replacement or repair of the tire very costly or very complicated.

Additional drawbacks to existing road condition detection systems include a limited sensing capability. While an estimated surface coefficient of friction may be detected, other data regarding the road condition, such as the type of surface, is not detected. Accordingly, there exists a need to provide a road recognition system with can easily be applied to both new and existing vehicles without altering the tire structure or requiring complicated structural enhancements, while also providing a robust detection system for supplying information regarding the road condition including the surface condition.

BRIEF SUMMARY OF THE INVENTION

The present invention provides an apparatus and method for detecting the road surface condition for use in a motor vehicle. The system and method detect road data through a temperature sensor, an ultrasonic sensor, and a camera. These sensors provide temperature data, roughness data, and image data, respectively. Subsequently, the road data is filtered for easier processing. A comparison of the filtered road data to reference data is made, and a confidence level of that comparison is generated. Based on the comparison of filter road data to reference data, the road service condition is determined. Finally, a reliability number of the road surface condition determination is made based on the confidence level.

Preferably, the driver is informed of the road surface condition when the reliability number is above a predetermined value. Similarly, stability control systems are optimized in accordance with the detected road surface condition when the reliability number is above a predetermined value. Filtering the road data can include compressing the image data. In turn, compression of the image data may be accomplished in many different ways, including utilizing edge detection, line detection, softening techniques and recognition of color and brightness. A threshold frequency can be employed for filtering ultrasonic data. An average of the ultrasonic data over a set period of time, or a Fourier transform, may be utilized.

The comparison of filtered road data to reference data may include determining an environmental classification of the road surface condition, such as dry, ice, snow, or water. A surface classification of the road surface condition may also be determined, such as concrete, asphalt, dirt, grass, sand, or gravel. The confidence level is determined by the correlation between the road data and reference data. Preferably, the reliability number is based not only on the confidence level, but also on the consistency of the road and filter data for a given period of time, and the amount of noise in the road data prior to filtering. The driver is preferably informed through images or text on a traditional display panel. Vehicle stability systems include such systems as interlock braking systems, traction control systems, yaw and roll stability systems and the like.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
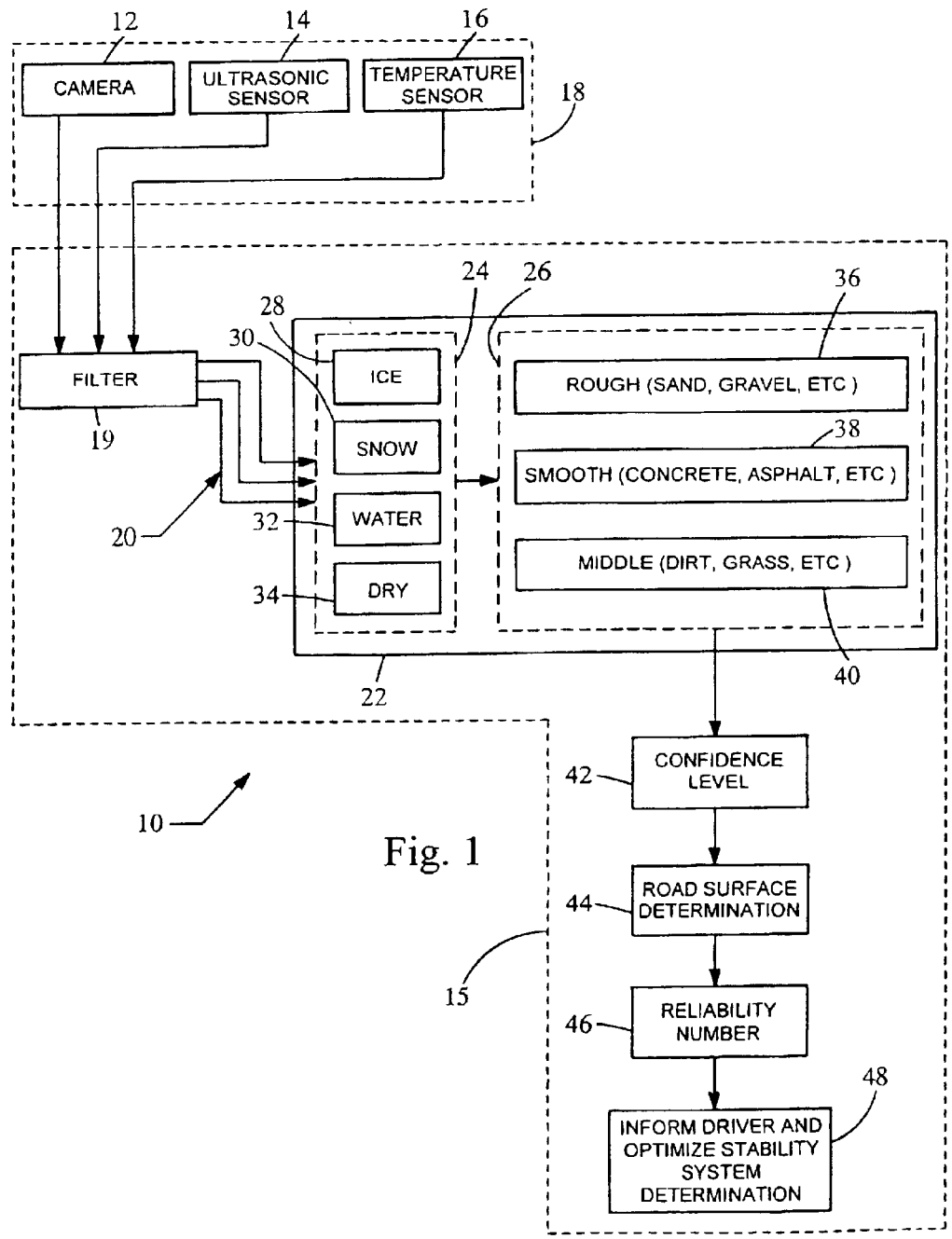
FIG. 1 is a schematic representation of an embodiment of the process for detecting the road surface condition in accordance with the teachings of the present invention.
Figure 2:
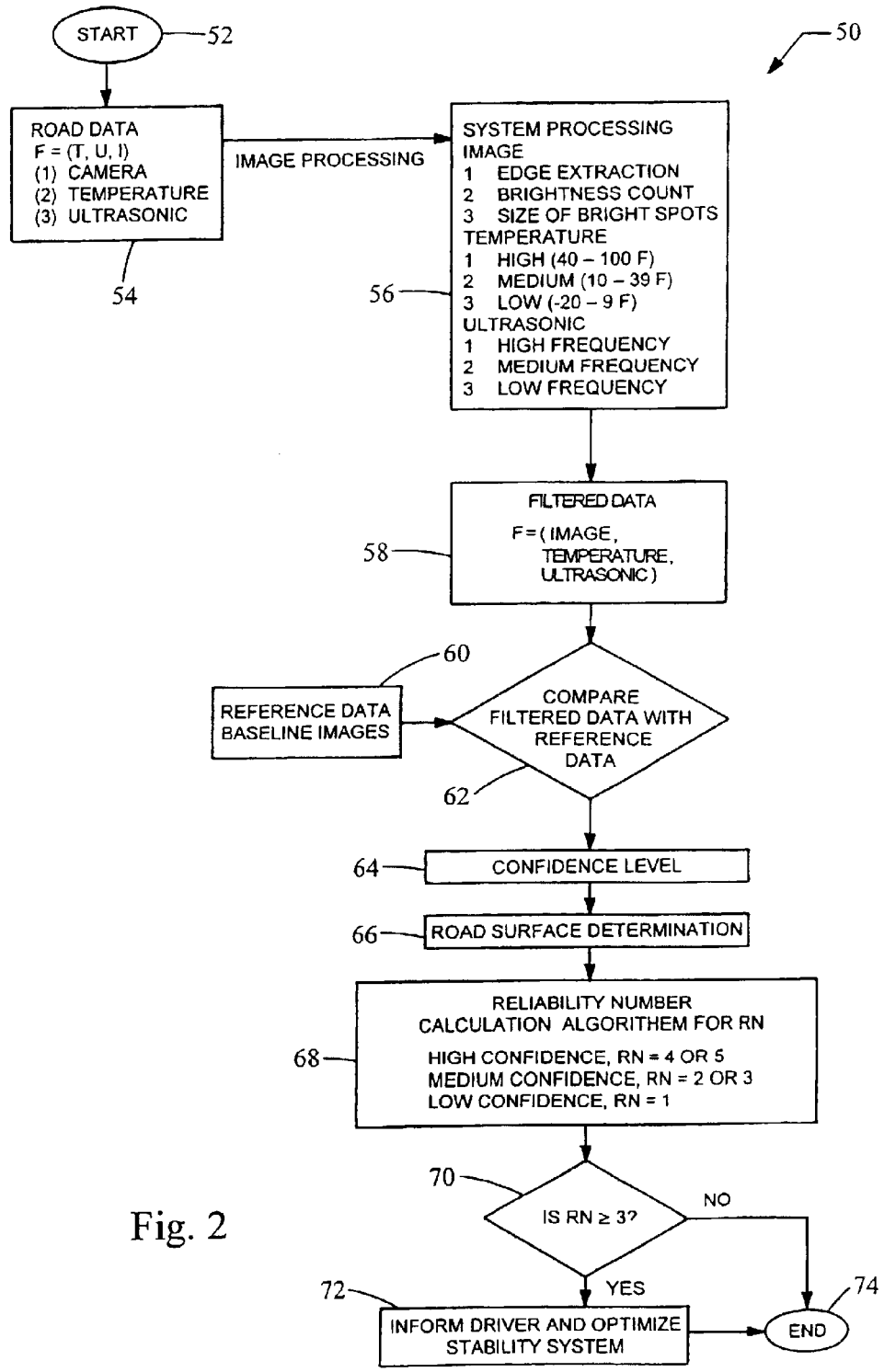
FIG. 2 is a logical flow chart of the process depicted in FIG. 1 showing the determination of the environmental classification of the road surface condition.

Turning now to the figures, the present invention provides a system 10 and process 50 for determining the road surface condition for a vehicle prior to entering the area or at the time of entering the area, as shown in FIGS. 1 and 2. Uniquely, a camera 12 is employed for recognizing the road condition. Knowing the road condition significantly increases the reliability of stability control systems and provides prompt feedback to the driver. That is, being able to recognize the road condition and surface condition, (including the surface coefficient of friction mu) also referred to herein to as mu, allows stability control systems such as anti-lock braking systems, traction control systems, roll and yaw stability systems, and integrated vehicle dynamics to be optimized to increase reliability and reaction time. For example, the anti-lock braking system can exclude certain software checks by knowing the surface condition is generally either high-mu or low-mu. This also removes the potential for misdetection by the anti-lock braking system software. Similarly, the transition between high to low mu, and vice versa, can be optimized for the integrated vehicle dynamics. Misdetection or erroneous estimation of surface condition (mu) based on lateral and longitudinal sensors also be eliminated.

The system and method 10 for detecting the road surface condition ahead of a motor vehicle will first be described broadly, and then followed by specific details of its aspects. With reference to FIG. 1, sensors provide raw road data 18 for road surface condition determination. The sensors preferably include a camera 12, ultrasonic sensor 14 and a temperature sensor 16. The road data 18 is filtered to form filtered data 20 for easier processing by the microprocessor or cpu 15. The filtered data 20 is then compared to reference data 22 which is stored in a database accessible by the microprocessor 15. Based on the closeness or exactness of the comparison of filtered data 20 to reference data 22, a confidence level 42 can be determined. Additionally, a road surface determination 44 is made based on the comparison of filtered data 20 reference data 22. A reliability number 46 is then generated, which is based, at least in part, on the confidence level 42. When the reliability number 46 is sufficient or meets a predetermined threshold, the driver may be informed and stability systems may be optimized, as indicated by block 48.

As shown in FIG. 1, the camera 12, ultrasonic sensor 14, and temperature sensor 16 provide image data, roughness data, and temperature data, respectively, to a microprocessor 15. This data collectively forms as road data 18. The camera 12 is preferably a digital camera, and may be mounted on a vehicle in a desired position to detect an image for recognition and determination of the road and surface condition. The camera may be placed in a wide variety of locations dependent upon the information that is required by the system 10. Preferably, the camera 12 is mounted to the front the vehicle for imaging ahead of the vehicle. The camera should be angled in such away that the road condition image would be taken before the vehicle encounters the imaged terrain. The temperature sensor 16 can be any sensor that is well known in the automobile art. For example, there are noncontact temperature sensors that output both road and air temperatures. The ultrasonic sensor 14 can also be selected from many known sensors, and generally includes a sending unit and a receiving unit for detecting the roughness by reading the frequency of the reflected ultrasonic signal. The sensor 14 should have a range from 6 to 10 feet and an accuracy of 0.1% over this range.

The road data 18 is the raw data collected from the camera 12, the ultrasonic sensor 14 and the temperature sensor 16. To provide for fast processing and handling of the road data 18, the data is filtered to form filtered data 20. More specifically, the image data from the camera 12 may be compressed utilizing various techniques. Edge detection techniques such as a gradient edge detection or laplacian edge detection may be employed. Likewise, line detection such as Sobel, Pewit, shift and difference, or line segment detection may be employed. Another compression technique includes softening the image to reduce noise, such as by utilizing an average filter, a medium filter, or a Gaussian filter. The image data could also be filtered to include only color recognition, and more specifically could simply detect brightness and the size of bright spots. The ultrasonic data is preferably filtered by taking an average of the data over time, or alternatively by utilizing a Fourier transform.

The filtered data 20 is then compared to reference data 22. The reference data 22 refers to data which is used as a baseline for road classification. This data is gathered during the development phase and provides numerous samples for all possible road classifications. Preferably, the reference data is divided into two groups including an environmental classification 24 and a surface classification 26. The environmental classification 24 includes ice 28, snow 30, water 32, and dry 34. The surface classifications include rough 36, smooth 38, and middle 40. Examples of rough 36 include sand and gravel. Examples of smooth 38 include concrete and asphalt. Examples of middle 40 include dirt and grass. The reference data 22 will also include a characterization of the surface condition (mu) based on the particular combination of environmental classification 24 and surface classification 26.

Logic flow chart has been depicted in FIG. 2 representing the method 50 for detecting the road surface condition. The process 50 begins at block 52 and flows to block 54 where road data 18 is captured. The road data 18 includes image data, temperature data and roughness data. The data is processed as indicated by block 56. More specifically, the image data is compressed and is filtered to include one or more variables. For example, the variables of edge extraction, brightness count, and size of bright spots may be utilized to represent the image data.

Figure 3A:
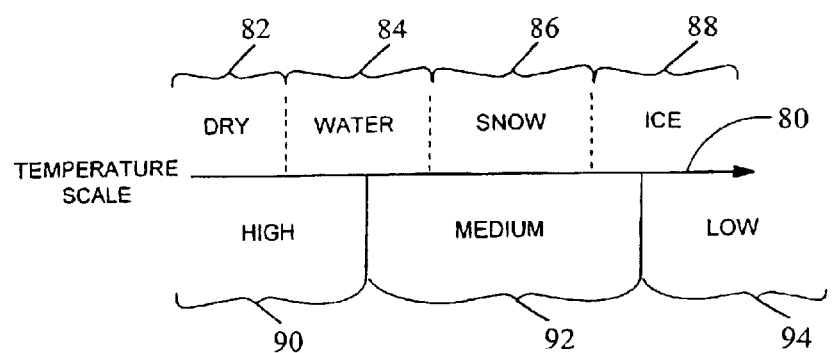
FIGS. 3a and 3b show a temperature scale and frequency scale, respectively, that is utilized by the system depicted in FIG. 1.

The temperature data may be filtered into a single variable such as "low" (−20 to 9° F.), "medium" (10 to 39° F.) and "high" (40 to 100° F.). As shown in FIG. 3a, a horizontal axis 80 represents a temperature scale along which the temperature data will lie. The temperature data may be filtered into three main groups including high 90, medium 92, and low 94. The high, medium and low groups, 90, 92, 94 correspond to certain environmental classifications 24. For example, when the temperature data is characterized as low 94 (the environmental classification will always be ice 88.) When the temperature data is characterized as high 90, the environmental classification of dry 82 or water 84 is appropriate, as snow and ice will not be found in high temperature 40 to 100° F. When the temperature data is characterized as medium 92, the environmental classification may be either water 84, snow 86, or ice 88.

Figure 3B:
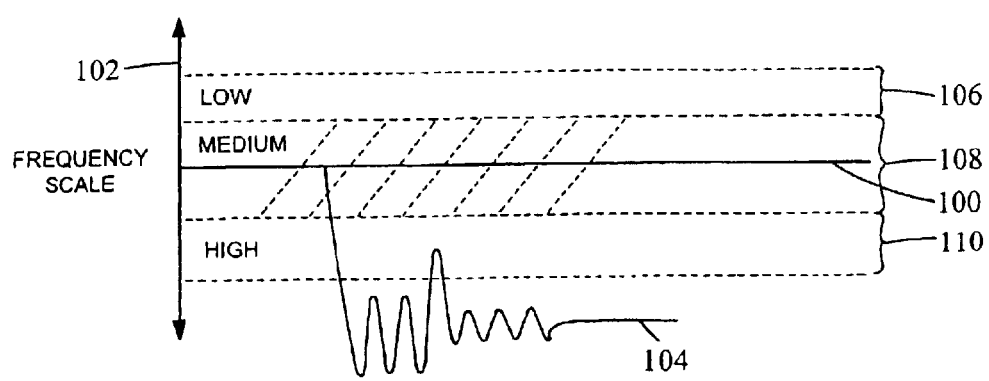

Similarly, the ultrasonic data may be filtered into a simple single variable representing "low", "medium" or "high" frequency. As shown in FIG. 3b, a graph of the ultrasonic or roughness data 104 can be made where the horizontal axis 100 represents time and the vertical axis 102 represents frequency. At any given time, the roughness data 104 can be characterized based on its frequency. Dash lines have been used to indicate the divisions between a low frequency 106, a medium frequency 108, and a high frequency 110. Generally, a low frequency 106 represents a smooth surface, while a high frequency 110 represents a rough surface. A medium frequency 108 represents a surface roughness somewhere between the smooth 106 and rough 110 values.

The resulting filtered data 58 is then compared to reference data 50 as indicated by determination block 62.

Based on the comparison step 62, a confidence level 64 is determined. The confidence level 64 will increase as the closeness of the comparison increases. For example, on a 0 to 5 scale, 5 may represent an exact data match, while 0 would represent an unrecognizable filter data set 58. With regard to the image data, each image would have a 'feature set', i.e., a vector where each element of the vector is a parameter of the image. Examples of parameters are scalars like center of gravity, moments, etc. The parameters of each data image are measured and its feature vector is created. Now this feature vector is compared with the feature vectors of all the reference data images. The closer this feature vector is to a particular feature vector of a reference image, the higher the correlation and hence the confidence value. There are many ways to determine the "closeness" of the vectors. The simplest is the "distance", i.e., a measurement of the distance between the feature vectors. The minimum distance is the measure of the closest match.

After the comparison step 62, a road surface determination is made as indicated by block 66. The mad surface determination 66 is an extrapolation from the reference data 60 based on the comparison 62 of the filtered and reference data. A reliability number 68 is then generated. The reliability number may be simply based on the confidence level 64. However, additional variables may be used in generating the reliability number, such as the consistency between the road data and the filtered data over a given period of time. Similarly, the amount of noise in the road data prior to filtering may also be utilized. Preferably, the confidence level 64 is the predominant factor in the reliability number determination 68. If the reliability number is greater than a predetermined value, say 3 on a scale of 0 to 5, the method 50 will inform the driver and optimize a stability system as indicated by block 72. If the reliability number does not meet a predetermined threshold, the method 50 will flow to its end at block 74.

Figure 4:
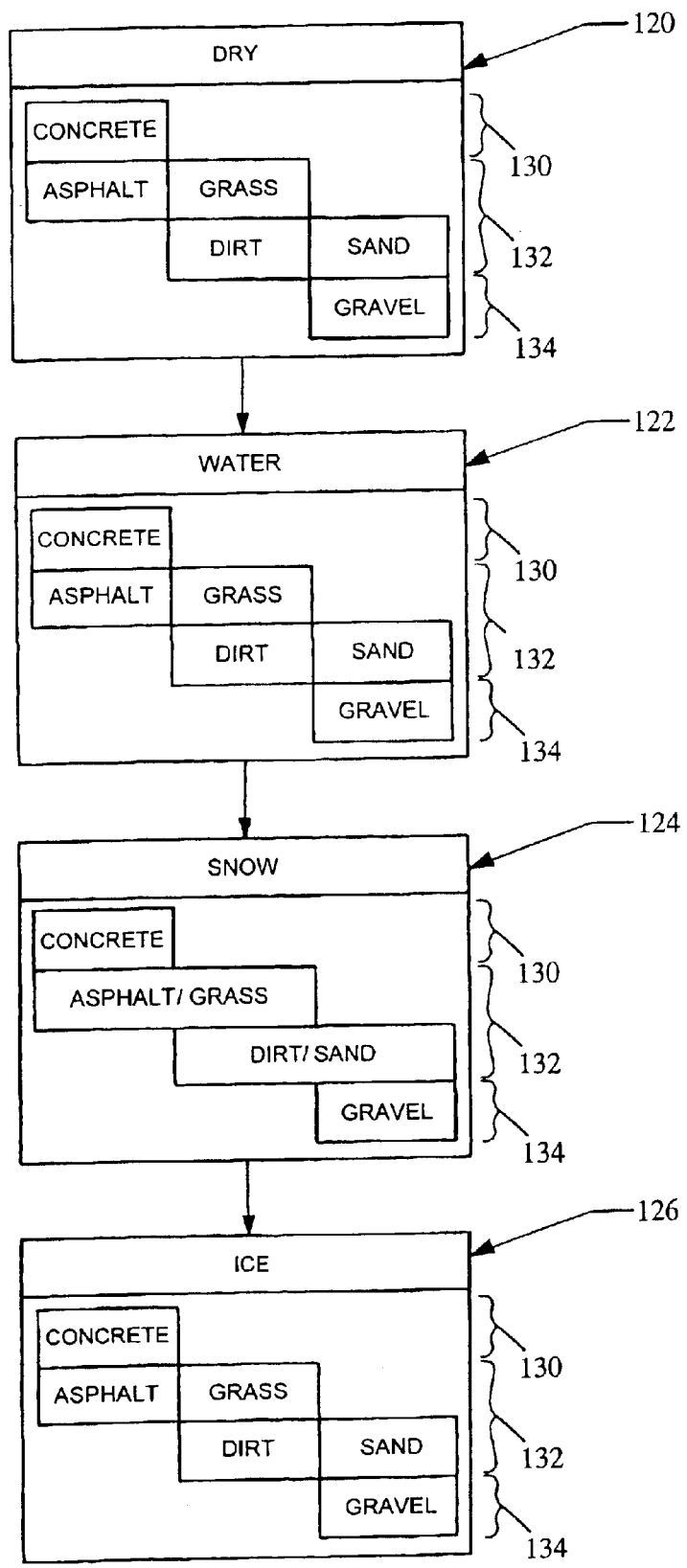
FIG. 4 shows a chart used in determining surface classification by the system depicted in FIG. 1.

Turning now to FIG. 4, the environmental and surface classification will be discussed. Once the filtered data 20 has been obtained, it is characterized by two classifications including an environmental classification 24 and a surface classification 26. First, the temperature data may be used to generally classify the environmental classification 24 as either dry 82, water 84, snow 86 or ice 88 as indicated in FIG. 3A. When the temperature data does not give a specific environmental classification, i.e., when the temperature data is filtered as either high 90 or low 92, the image data is then used to make the environmental classification 24. As previously discussed, this is accomplished by comparing the image data to reference image data, preferably through correlation and/or feature vectors.

Once the environmental classification 24 has been made based on the temperature and image data, a surface classification 26 is made. As shown in FIG. 4, numerous lookup charts may be employed. More specifically, a dry chart 120, a water chart 122, and snow chart 124, and an ice chart 126 may be employed. Using these charts 120, 122, 124 and 126, the ultrasonic data and image data are employed to make the surface classification 26.

First the roughness data is analyzed. It can be seen that for all environmental classifications, when the ultrasonic or roughness data is classified as low 130, the surface classification of "concrete" can be made. Likewise, when the ultrasonic or roughness data has been classified as high 134, the surface classification 26 of "gravel" may be made. However, when the roughness data is classified as medium 132, the system 10 and method 50 must still distinguish between asphalt, grass, dirt and sand. Accordingly, image data, which is preferably filtered into edge or line extraction, color recognition or brightness recognition, is compared to reference image data in order to further define between the surface classifications. Alternatively, in every environmental classification 24, the filtered roughness data may be compared to reference roughness data and the filtered image data may be compared to reference image data in order to determine a surface classification.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for detecting the road condition for use in a motor vehicle, the method comprising the steps of:

detecting road data through a temperature sensor providing temperature data, an ultrasonic sensor providing roughness data, and a camera providing image data;

filtering the road data for processing;

comparing filtered road data to reference data and generating a confidence level of the comparison;

determining a road surface condition based on the comparison of filtered road data to reference data; and determining a reliability number of the road surface condition determination based on the confidence level.

2. The method of claim 1, further comprising the step of informing the driver of the road surface condition when the reliability number is above a predetermined value.

3. The method of claim 1, further comprising the step of optimizing stability control systems of the vehicle in accordance with the detected road surface condition when the reliability number is above a predetermined value.

4. The method of claim 1, wherein the step of filtering road data includes employing a threshold frequency for ultrasonic data.

5. The method of claim 1, wherein the step of filtering road data includes taking an average of the ultrasonic data.

6. The method of claim 1, wherein the step of filtering road data includes applying a Fourier transform to the ultrasonic data.

7. The method of claim 1, wherein the step of determining a reliability number relies predominately on the comparison of the filtered and reference road data.

8. The method of claim 1, wherein the step of determining a reliability number incorporates the consistency of the road and filtered data for a given period of time.

9. The method of claim 1, wherein the step of determining a reliability number incorporates the amount of noise in the road data prior to filtering.

10. The method of claim 1, wherein the temperature sensor provides air temperature data and road temperature data.

11. A method for detecting the road condition for use in a motor vehicle, the method comprising the steps of:

detecting road data through a temperature sensor providing temperature data, an ultrasonic sensor providing roughness data, and a camera providing image data;

filtering the road data for processing, including compressing the image data;

comparing filtered road data to reference data and generating a confidence level of the comparison;

determining a road surface condition based on the comparison of filtered road data to reference data; and determining a reliability number of the road surface condition determination based on the confidence level.

12. The method of claim 11, wherein compressing image data includes utilizing edge detection.

13. The method of claim 11, wherein compressing image data include utilizing line detection.

14. The method of claim 11, wherein compressing image data includes softening the image to reduce noise.

15. The method of claim 11, wherein compressing image data includes recognizing color.

16. A method for detecting road condition for use in a motor vehicle, the method comprising the steps of:

detecting road data through a temperature sensor providing temperature data, an ultrasonic sensor providing roughness data, and a camera providing image data;

filtering the road data for processing;

comparing filtered road data to reference data and generating a confidence level of the comparison;

determining a road surface condition, including an environment classification of road surface condition, based on the comparison of filtered road data to reference data; and determining a reliability number of the road surface condition determination based on the on the confidence level.

17. The method of claim 16, wherein the step of determining an environment classification includes:
   establishing a temperature of the air and the road;
   selecting a portion of the reference data based on the temperature data;
   comparing roughness data from the ultrasonic sensor to the selected portion of the reference data; and
   comparing image data from the camera to the selected portion of the reference data.

18. A method for detecting the road condition for use in a motor vehicle, the method comprising the steps of:
   detecting road data through a temperature sensor providing temperature data, an ultrasonic sensor providing roughness data, and a camera providing image data;
   filtering the road data for processing;
   comparing filtered road data to reference data and generating a confidence level of the comparison;
   determining a road surface condition, including a surface classification of road surface condition, based on the comparison of filtered road data to reference data; and
   determining a reliability number of the road surface condition determination based on the confidence level.

19. The method of claim 18, wherein the step of determining a surface classification first compares roughness data from the ultrasonic sensor and then compares image data from the camera to increase the confidence level.

20. A road condition detection system for a motor vehicle, the detection system comprising:
   means for detecting road data through a temperature sensor providing temperature data, an ultrasonic sensor providing roughness data, and a camera providing image data;
   means for filtering road data for easier processing;
   means for comparing filtered road data to reference data and generating a confidence level of the comparison;
   means for determining a road surface condition, including one of an environmental classification and a surface classification of road surface condition, based on the comparison of filtered road data to reference data; and
   means for determining a reliability number of the road surface condition determination based on the confidence level.

21. The method of claim 20, wherein the filtering means compresses the image data.

* * * * *

UNITED STATES PATENT AND TRADEMARK OFFICE
CERTIFICATE OF CORRECTION

PATENT NO. : 6,807,473 B1
DATED : October 19, 2004
INVENTOR(S) : Vinh H. Tran

It is certified that error appears in the above-identified patent and that said Letters Patent is hereby corrected as shown below:

Column 6,
Line 55, after "detecting" insert -- the --.

Column 7,
Line 3, delete "on the" (second occurrence).

Signed and Sealed this

Twenty-second Day of February, 2005

JON W. DUDAS
*Director of the United States Patent and Trademark Office*